(12) United States Patent
Hong et al.

(10) Patent No.: US 11,614,389 B2
(45) Date of Patent: Mar. 28, 2023

(54) AUTOMATED APPARATUS FOR SAMPLE PYROLYSIS

(71) Applicant: LG Chem, Ltd., Seoul (KR)

(72) Inventors: Sungwon Hong, Daejeon (KR); Kyungmee Lee, Daejeon (KR); Jeong Ae Ahn, Daejeon (KR); Nak Hee Choi, Daejeon (KR)

(73) Assignee: LG Energy Solution, Ltd.

( * ) Notice: Subject to any disclaimer, the term of this patent is extended or adjusted under 35 U.S.C. 154(b) by 554 days.

(21) Appl. No.: 16/500,264

(22) PCT Filed: Dec. 4, 2018

(86) PCT No.: PCT/KR2018/015214
§ 371 (c)(1),
(2) Date: Oct. 2, 2019

(87) PCT Pub. No.: WO2019/112276
PCT Pub. Date: Jun. 13, 2019

(65) Prior Publication Data
US 2020/0072715 A1    Mar. 5, 2020

(30) Foreign Application Priority Data

Dec. 4, 2017    (KR) ......................... 10-2017-0164993
Dec. 3, 2018    (KR) ......................... 10-2018-0153259

(51) Int. Cl.
*G01N 1/44*    (2006.01)
*G01N 1/22*    (2006.01)
(Continued)

(52) U.S. Cl.
CPC ............. *G01N 1/44* (2013.01); *G01N 1/2226* (2013.01); *G01N 1/4022* (2013.01);
(Continued)

(58) Field of Classification Search
CPC ....... G01N 1/44; G01N 1/2226; G01N 1/4022
See application file for complete search history.

(56) References Cited

U.S. PATENT DOCUMENTS 3,955,924 A    5/1976    Northmore et al.
4,798,805 A    1/1989    Issenmann
(Continued)

FOREIGN PATENT DOCUMENTS

CN    1623089 A    6/2005
CN    101846642 A    9/2010
(Continued)

OTHER PUBLICATIONS

Extended European Search Report including Written Opinion for Application No. EP18885613.2, dated May 6, 2020, pp. 1-10.
(Continued)

*Primary Examiner* — Brian R Gordon
*Assistant Examiner* — Dwan A Gerido
(74) *Attorney, Agent, or Firm* — Lerner, David, Littenberg, Krumholz & Mentlik, LLP (57) ABSTRACT

An apparatus for generating gas from a sample (battery) by pyrolysis of the sample in order to collect or analyze gas generated inside the sample due to the thermal behaviors of the sample. More specifically, provided is an apparatus wherein not only gas generated due to the thermal behaviors of a sample (battery) can be generated by heating the sample (battery itself), but also a series of processes provided to collect or analyze the generated gas can be automatically controlled.

11 Claims, 6 Drawing Sheets

(51) Int. Cl.
G01N 1/40 (2006.01)
H01M 10/42 (2006.01)

(52) U.S. Cl.
CPC .............. H01M 10/4285 (2013.01); *G01N 2001/2241* (2013.01); *G01N 2001/4033* (2013.01)

(56) References Cited

U.S. PATENT DOCUMENTS

| | | | |
|---|---|---|---|
| 6,617,164 | B1 | 9/2003 | Avakgharagelou |
| 9,027,421 | B2 | 5/2015 | Gellert |
| 2003/0049854 | A1* | 3/2003 | Rhodes .............. G01N 33/0014 422/62 |
| 2005/0175510 | A1 | 8/2005 | Marabini et al. |
| 2007/0284523 | A1* | 12/2007 | May ....................... G01N 1/405 250/288 |
| 2009/0159504 | A1* | 6/2009 | Choi ........................ C10G 9/00 208/254 R |
| 2012/0035403 | A1* | 2/2012 | Flytzani-Stephanopoulos ............ C07C 1/2078 585/240 |
| 2014/0241394 | A1 | 8/2014 | Olson |
| 2019/0047863 | A1* | 2/2019 | Cook .................... C01B 32/152 |

FOREIGN PATENT DOCUMENTS

| | | |
|---|---|---|
| CN | 103018376 A | 4/2013 |
| CN | 102667464 B | 2/2014 |
| CN | 104483423 A | 4/2015 |
| CN | 206512150 U | 9/2017 |
| EP | 3242130 A1 | 11/2017 |
| JP | S50131586 A | 10/1975 |
| JP | S5417792 B2 | 7/1979 |
| JP | H02035328 A | 2/1990 |
| JP | H06082434 A | 3/1994 |
| JP | 2000258309 A | 9/2000 |
| JP | 3191147 B2 | 7/2001 |
| JP | 2003065958 A | 3/2003 |
| JP | 2005-024525 A | 1/2005 |
| JP | 2005024525 * | 1/2005 |
| JP | 2006226746 A | 8/2006 |
| JP | 2013-011452 A | 1/2013 |
| JP | 2013015387 A | 1/2013 |
| JP | 2014-507652 A | 3/2014 |
| JP | 2014-182037 A | 9/2014 |
| JP | 2017181212 A | 10/2017 |
| KR | 1348540 B1 | 8/2008 |
| KR | 2011-0018511 A | 2/2011 |
| KR | 101116364 B1 | 3/2012 |
| KR | 1168826 B1 | 7/2012 |
| KR | 2012-0124830 A | 11/2012 |
| KR | 2016-0139615 A | 12/2016 |
| KR | 20160139165 A | 12/2016 |
| KR | 1744462 B1 | 5/2017 |
| KR | 2017-0122552 A | 11/2017 |
| RU | 2516548 C2 | 5/2014 |
| WO | 2014-178147 A1 | 11/2014 |

OTHER PUBLICATIONS

International Search Report in PCT/KR2018/015214, dated Mar. 28, 2019, 2 pages, with English Translation.
Chinese Search Report for Application No. 201880015917.5, dated Jun. 30, 2021, 3 pages.
Search Report dated Feb. 23, 2022 from the Office Action for Chinese Application No. 201880015917.5 dated Mar. 3, 2022, pp. 1-2.

* cited by examiner

AUTOMATED APPARATUS FOR SAMPLE PYROLYSIS

CROSS-REFERENCE TO RELATED APPLICATIONS

The present application is a national phase entry under 35 U.S.C. § 371 of International Application No. PCT/KR2018/015214 filed Dec. 4, 2018, published in Korean, which claims priority from Korean Patent Application No. 10-2017-0164993, filed on Dec. 4, 2017, and Korean Patent Application No. 10-2018-0153259, filed on Dec. 3, 2018, all of which are incorporated herein by reference.

TECHNICAL FIELD

The present invention relates to a device for generating gas from a sample for collecting or analyzing the gas generated in the sample according to the thermal behavior (temperature-rising process, isothermal process, etc.) of the sample, and more specifically, to a device in which gas can be generated according to the thermal behavior of a sample by heating the sample (for example, battery itself) and a series of processes that are provided to collect or analyze the gas generated can be controlled automatically.

BACKGROUND ART

Generally, there is a problem about the safety of a secondary battery such as an ignition and explosion of a lithium ion battery in recent. There are many reasons for this. Among them, a large amount of gas is generated from the structure collapse and electrolytic decomposition of the cathode material due to the pyrolysis in the battery, thereby increasing the internal pressure of the battery, resulting in a series of phenomena such as swelling, explosion and ignition of the battery, and it is one of the causes of the ignition and explosion of the lithium ion battery.

On the other hand, as a conventional technique, an Evolved Gas Analysis (EGA) method is a technique for analyzing the gas generated by pyrolysis of a sample using a pyrolyzer, and there is a device for analyzing the gas generated by taking a battery material of about 10 mg or less and pyrolyzing it, such as a conventional Evolved Gas Analysis-Mass Spectrometer (EGA-MS).

Further, in the conventional technique for evaluating the thermal characteristics of a battery, there is an Accelerating Rate Calorimeter (ARC) as a device for measuring the calories of the battery, and this is an accelerating rate calorimeter that accurately measures the exothermic onset to measure the thermal stability of the battery in an adiabatic environment.

SUMMARY

Technical Problem

The above-described conventional technique is applicable only when a small amount of solid and liquid samples are preset, and it is difficult to grasp the gas generation characteristics according to the thermal behavior of the battery itself. Therefore, it is required to develop a new device for collecting and analyzing the internally generated gas according to the thermal behavior of the battery itself. That is, a new concept device capable of analyzing the gas generated according to the thermal behavior of the battery itself, which is not applicable to the conventional pyrolysis analysis method (TPD-MS, etc.), is required.

Technical Solution

The automated sample pyrolysis device according to one embodiment of the present invention, which can be connected to the front of the gas analyzer or gas collector to collect or analyze the gas generated by the heating of a sample, may be characterized by comprising:

a reactor, in which the sample is automatically accommodated; and a furnace capable of surrounding the reactor and capable of heating the sample, wherein carrier gas is automatically supplied into the reactor from the start of operation of the automated sample pyrolysis device until the first predetermined condition is satisfied, in the second predetermined condition, the gas generated in the sample is automatically supplied to the gas analyzer or the gas collector, in the third predetermined condition, the supply of the carrier gas into the reactor is automatically stopped and the supply of the gas generated from the sample in the reactor to the gas analyzer or the gas collector is automatically stopped.

Advantageous Effects

According to the present invention, it is possible to collect or analyze the gas generated in a sample (for example, battery itself) according to the thermal behavior of the sample, and the process of pyrolyzing the sample (battery itself) to collect and measure the gas generated in the battery is automated. This is, quite different from the conventional devices and methods for collecting the gas generated in a secondary battery. It can collect the gas generated in the sample (battery) according to the thermal behavior of the sample and analyze it more precisely in real time, and it has the advantage of safely protecting the operators from the danger of battery ignition or explosion. In addition, it has an advantage of collecting or analyzing all the gas generated in the sample (battery) such as electrolytic decomposition gas as well as $O_2$, $CO_2$, $H_2O$ and CO generated in the sample (battery material).

DETAILED DESCRIPTION

Various changes in form and details may be made to the presently disclosed embodiment and thus should not be construed as being limited to the aspects set forth herein. The presently disclosed embodiment is not limited to the aspects described in the present description, and thus it should be understood that the presently disclosed embodiment includes every kind of variation example or alternative equivalent included in the spirit and scope of the presently disclosed embodiment. Also, while describing the aspects, detailed descriptions about related well-known functions or configurations that may diminish the clarity of the points of the aspects of the presently disclosed embodiment will be omitted.

The automated sample pyrolysis device according to one embodiment of the present invention, which can be adapted to be connected to a front of a gas analyzer or gas collector to collect or analyze the gas generated by the heating of a sample, may comprise:

a reactor adapted to accommodate the sample; a furnace capable of surrounding the reactor and capable of heating the sample, and a main controller that may be configured to automatically control a supply of a carrier gas into the reactor from a start of operation of the automated sample pyrolysis device until a first predetermined condition is satisfied, when second predetermined condition is satisfied, control a supply of the gas generated by heating of the sample to the gas analyzer or the gas collector, when third predetermined condition is satisfied, control both the supply of the carrier gas into the reactor and the supply of the gas generated by heating of the sample in the reactor to the gas analyzer or the gas collector to be stopped.

Further, the automated sample pyrolysis device according to one embodiment of the present invention may be configured to, when the first predetermined condition is satisfied, automatically stop the supply of the carrier gas into the reactor, and when the second predetermined condition is satisfied, automatically start the supply of the carrier gas into the reactor.

Further, in the automated sample pyrolysis device according to one embodiment of the present invention may be configured to, when the first predetermined condition and the second predetermined condition are the same, and when the first predetermined condition is satisfied, maintain the supply of the carrier gas into the reactor, and automatically supply the gas generated by heating of the sample in the reactor to the gas analyzer or the gas collector.

Further, in the automated sample pyrolysis device according to one embodiment of the present invention, the first predetermined condition may be that a first predetermined amount of time elapses from a start of the supply of the carrier gas to the reactor.

Further, in the automated sample pyrolysis device according to one embodiment of the present invention, the second predetermined condition may be that the furnace reaches a first predetermined temperature or a second predetermined amount of time elapses after the furnace reaches the first predetermined temperature.

Further, in the automated sample pyrolysis device according to one embodiment of the present invention, the first predetermined condition and the second predetermined condition may be the same, and the second predetermined condition may be that the first predetermined amount of time elapses from the start of the supply of the carrier gas.

Further, in the automated sample pyrolysis device according to one embodiment of the present invention, the third predetermined condition may be that the furnace reaches a second predetermined temperature, or that a third predetermined amount of time elapses after the start of the supply of the gas generated by heating of the sample in the reactor to the gas analyzer or the gas collector.

Further, the automated sample pyrolysis device according to one embodiment of the present invention may further comprise a carrier gas open/close means switchable between an open state and a closed state for controlling the entry of the carrier gas into the reactor;

an analyzer open/close means switchable between an open state and a closed state for controlling a flow of gas from the reactor into the gas analyzer or the gas collector; and a vent open/close means switchable between an open state and a closed state for regulating a discharge of gas from the reactor to outside of the automated sample pyrolysis device.

Further, in the automated sample pyrolysis device according to one embodiment of the present invention, the main controller may be configured to control the carrier gas open/close means and the vent open/close means to be in the open state and the analyzer open/close means to be in the closed state from the start of operation of the automated sample pyrolysis device until the first predetermined condition is satisfied, and the main controller is configured to switch the vent open/close means to the closed state when the first predetermined condition is satisfied.

Further, in the automated sample pyrolysis device according to one embodiment of the present invention, the main controller may be configured to switch the carrier gas open/close means to the closed state when the first predetermined condition is satisfied, and the main controller may be configured to switch the carrier gas open/close means and the analyzer open/close means to the open state when the second predetermined condition is satisfied.

Further, in the automated sample pyrolysis device according to one embodiment of the present invention, the first predetermined condition and the second predetermined condition may be the same, and the main controller may be configured to keep the carrier gas open/close means in the open state and to switch the analyzer open/close means to the open state when the first predetermined condition is satisfied.

Further, in the automated sample pyrolysis device according to one embodiment of the present invention, the main controller may be configured to switch the carrier gas open/close means and the analyzer open/close means to the closed state, and to switch the vent open/close means to the open state when the third predetermined condition is satisfied.

Further, the automated sample pyrolysis device according to one embodiment of the present invention may further comprise a cooling gas open/close means for controlling a flow of cooling gas to the reactor for cooling the reactor, and the main controller may be configured to switch the cooling gas open/close means to the open state when the third predetermined condition is satisfied.

Further, the automated sample pyrolysis device according to one embodiment of the present invention may further comprise a mass flow controller, located between the reactor and the carrier gas open/close means, for controlling a flow rate of the carrier gas supplied to the reactor.

Further, the automated sample pyrolysis device according to one embodiment of the present invention may further comprise a vent gas regulator, located between the reactor and the vent open/close means, for regulating a flow rate of the discharge of gas from the reactor to outside of the automated sample pyrolysis device.

Further, in the automated sample pyrolysis device according to one embodiment of the present invention, upper and lower ends of the reactor may be open, the reactor may further comprise a reactor top member and a reactor bottom member which are positioned near the open upper and lower ends of the reactor and may be capable of vertically transferring the sample, the reactor top member and the reactor bottom member may be vertically movable through the open upper and lower ends of the reactor, respectively, and one end of the reactor top member and one end of the reactor bottom member may be capable of sealing the reactor, and one end of the reactor, one end of the reactor top member and one end of the reactor bottom member may be capable of constituting a sealed chamber.

Further, the automated sample pyrolysis device according to one embodiment of the present invention may further comprise an automatic sample supply member capable of storing the sample and automatically supplying the sample, and a sample injection unit for transferring the sample from the automatic sample supply member to the reactor.

Further, in the automated sample pyrolysis device according to one embodiment of the present invention, one end of each of the reactor top member and the reactor bottom member may be coupled to a spring, and each of the reactor top member and the reactor bottom member may be vertically movable by an air cylinder connected to the spring.

Further, the automated sample pyrolysis device according to one embodiment of the present invention may further comprise a condenser, located between the reactor and the cooling gas open/close means, for cooling the gas in the reactor discharged from the reactor to the outside of the automated sample pyrolysis device.

Hereinafter, the automated sample pyrolysis device according to the present invention for automatically collecting or measuring the gas generated from the sample will be explained in detail. The accompanying drawings are provided for illustration only and should not be construed as limiting the scope of the invention.

In addition, the same or corresponding components are given by the same or similar reference numerals, regardless of the reference numerals in the drawings, for which the repeated explanation will be omitted, and for convenience of description, the size and shape of each illustrated structural member may be exaggerated or downsized.

Figure 1:
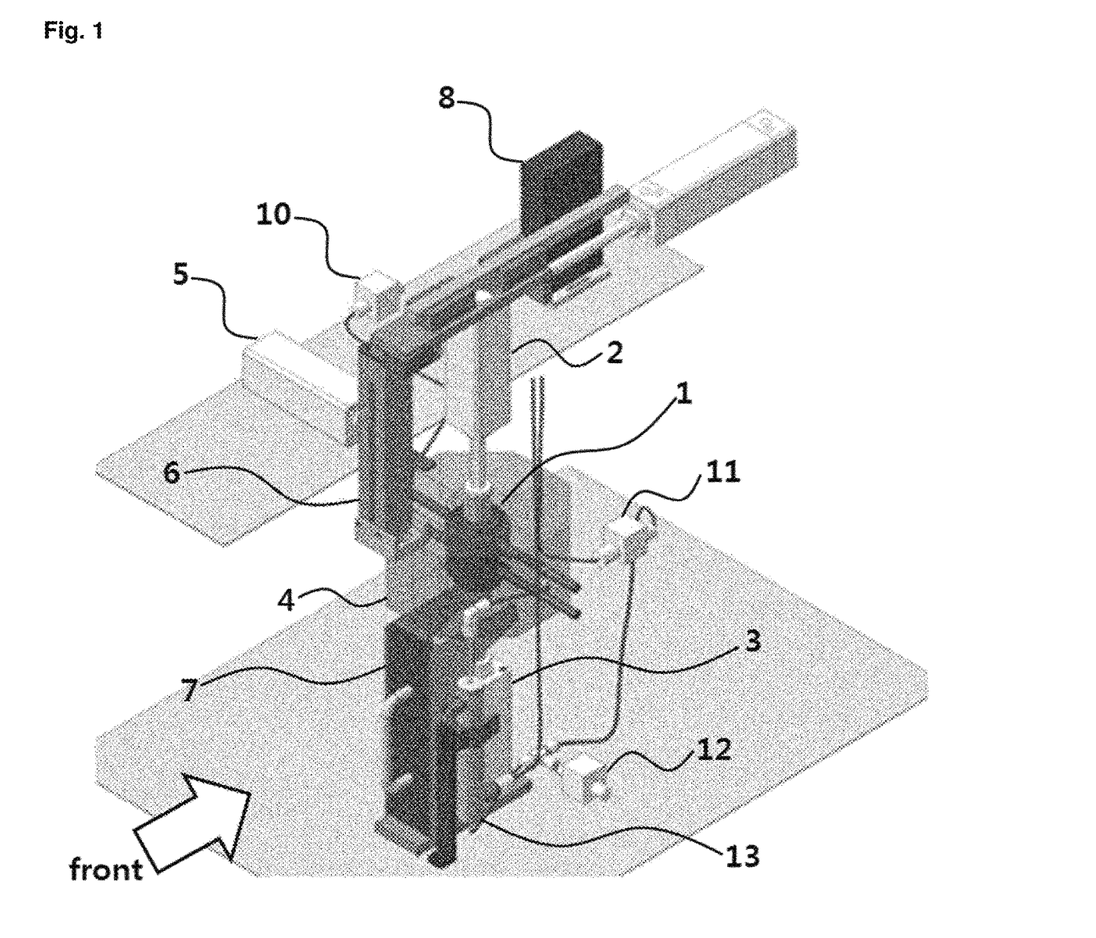
FIG. 1 and FIG. 2 show a front perspective view and a rear perspective view of the automated sample pyrolysis device of the present invention, respectively.
Figure 2:
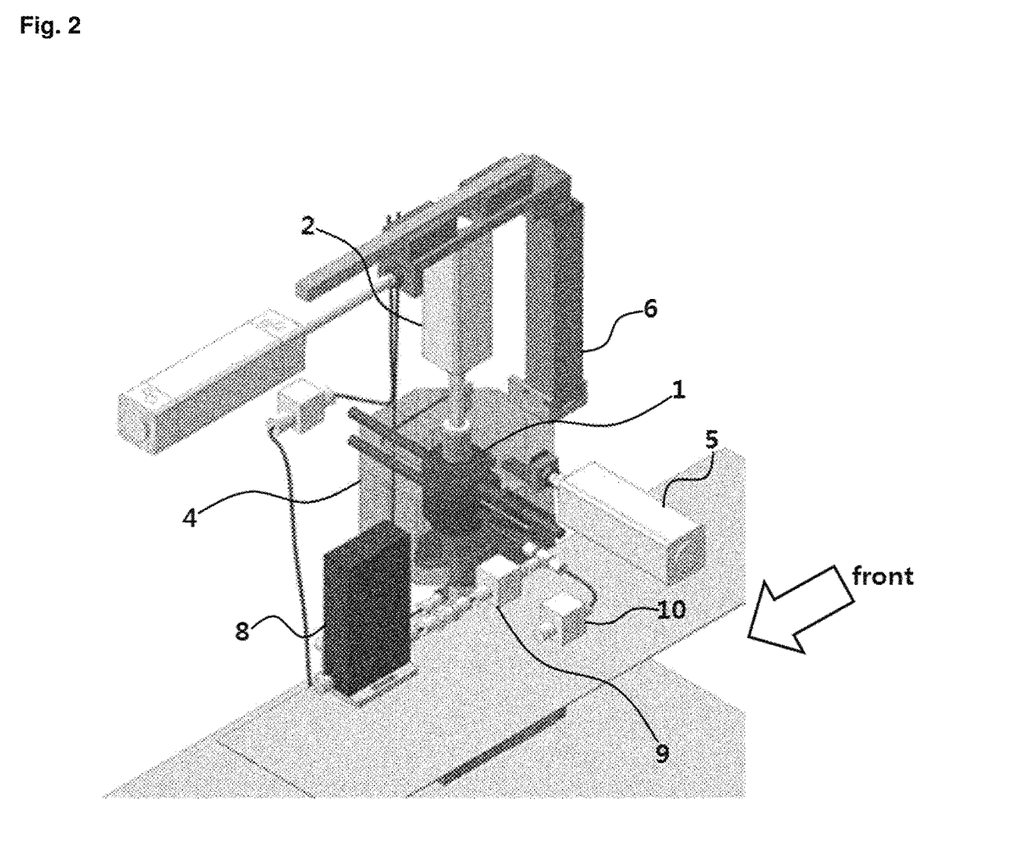

FIG. 1 and FIG. 2 show a front perspective view and a rear perspective view of the automated sample pyrolysis device according to one embodiment of the present invention for automatically collecting and measuring the gas generated in the sample (for example, battery) (Hereinafter, called "automated sample pyrolysis device") 100, respectively. In the drawings, corresponding elements are denoted by the same reference numerals, but in order to facilitate understanding in the drawings, some of the elements may be omitted or the positions may be partially changed.

First, in the automated sample pyrolysis device 100 according to one embodiment of the present invention, in order to collect and measure the gas generated in the sample according to the thermal behavior of the sample, the sample itself is heated inside the pyrolyzer, reactor 1, to collect the gas generated in the sample. In order to heat the sample accommodated in the reactor 1, a furnace 4 may surround the side of the reactor 1, and the upper and lower ends of the reactor 1 may be open. The reactor 1 may further comprise a reactor top member 2 and a reactor bottom member 3. The reactor top member 2 and the reactor bottom member 3 may be positioned near the open upper and lower ends of the reactor 1, respectively. The reactor top member 2 and the reactor bottom member 3 may comprise a spring, respectively, and the springs of the reactor top member 2 and the reactor bottom member 3 are connected to an air cylinder, respectively. Therefore, as a result of the operation of the air cylinder, the reactor top member 2 and the reactor bottom member 3 can move through the open upper and lower ends of the reactor 1, and can be controlled to accommodate the sample in the reactor 1 as described later (see, FIG. 3a and FIG. 3b). Further, one end of each of the reactor top member 2 and the reactor bottom member 3 is connected to the air cylinder and the shape thereof corresponds to the shape of the open upper and lower ends of the reactor 1. Accordingly, the reactor top member 2 and the reactor bottom member 3 can be moved to the open upper and lower ends of the reactor 1 and can be combined to the reactor 1 to seal the reactor 1. That is, the reactor 1, one end of the reactor top member 2 and one end of the reactor bottom member 3 are capable of constituting a sealed chamber. The reactor 1, one end of the reactor top member 2 and one end of the reactor bottom member 3 can be made of, for example, inconel or stainless steel (for example, SUS 310, 304, etc.). The reactor 1, the reactor top member 2 and the reactor bottom member 3 function as heat transfer, sealing and explosion proof to the sample contained in the reactor 1 from the furnace 4 during sample heating, and can withstand high temperature (for example, 600° C.). The spring of the reactor top member 2 and the spring of the reactor bottom member 3 may be made of, for example, Cr—Si alloy steel, and the maximum load thereof may be 50 kgf. The maximum load mass of each of the air cylinders connected to each spring of the reactor top member 2 and the reactor bottom member 3 may be 80 kg.

The furnace 4 surrounds the side of the reactor 1. The furnace 4 can heat the sample accommodated in the reactor 1 and can be controlled precisely at 1° C./min. The furnace 4 may be, for example, a Kanthal heater, and the outside of the furnace 4 may be surrounded by an insulating material to prevent heat loss to the outside during sample heating. The furnace 4 can raise or maintain the temperature of the reactor 1. Various methods for raising or maintaining the temperature of the reactor 1 can be set, and the temperature raising rate and the holding time can be variously set. For example, as the temperature of the reactor 1 is raised to 100° C. at a rate of 10° C. per minute or at a rate of 100° C., the temperature raising rate can be controlled, and as the temperature of the reactor 1 is kept at 100° C. for 1 hour or 2 hours and then the temperature of the reactor 1 is raised, the temperature of the reactor 1 may be kept at a constant temperature. The shape of the furnace 4 may be a regular octagonal columnar shape surrounding the cylindrical reactor 1 as shown in FIG. 1 and FIG. 2. However, the shape, material and the like of each of the reactor 1 and the furnace 4 of the present invention are not limited to those described above, and various modifications and changes can be made, for example, in the form of a cylinder or a square column. A terminal box is provided near the furnace, and the terminal box is the part containing the electrical wire that controls the furnace 4.

In the vicinity of the reactor 1 and the furnace 4 surrounding the reactor 1, there are provided a sample injection unit 5 capable of transferring the sample from the automatic sample supply member 6 described later into the reactor 1, and the automatic sample supply member 6 can be located. An air cylinder can be connected to the sample injection unit 5 for movement of the sample injection unit 5. For example, the sample injection unit 5 can move horizontally along the upper end of the furnace 4 on the upper end from the automatic sample supply member 6 to the upper end of the reactor 1 so as to transfer the sample (for example, one battery) into the reactor 1 surrounding the furnace 4. In addition, it may move in the vertical direction in some cases. The present invention is not limited to the above description, and various modification and changes can be made, for example, as the sample injection unit 5 can move from the point where the operator is located to the reactor 1 surrounded by the furnace 4. The maximum load mass of each of the air cylinders connected to the sample injection unit 5 may be 80 kg.

The automatic sample supply member 6 can accommodate at least one battery (for example, coin cell battery stack) as a sample, and can automatically supply the battery to the sample injection unit 5 according to a predetermined time or the like. The automatic sample supply member 6 can be made, for example, aluminum and the like.

Figure 3A:
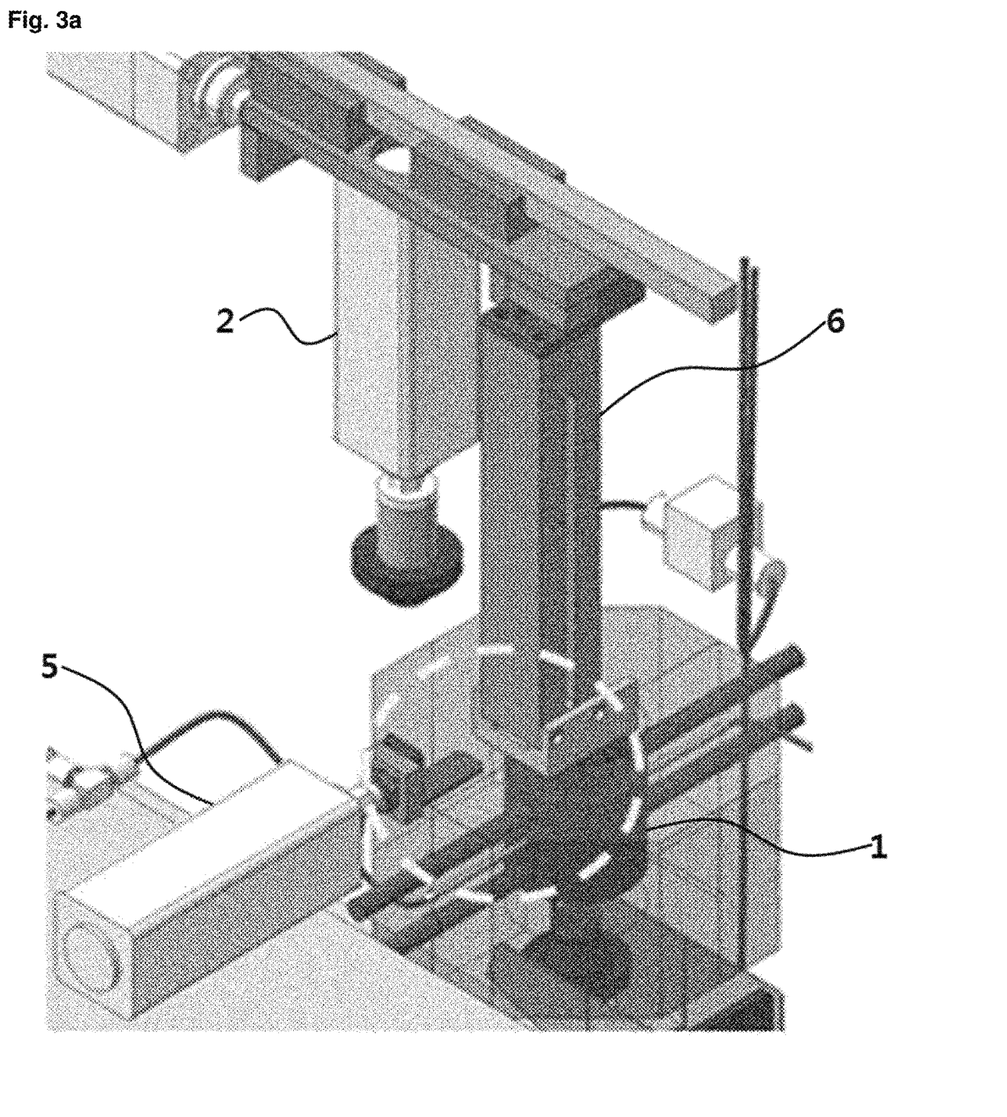
FIGS. 3a and 3b show a case in which a sample is accommodated in a reactor in the automated sample pyrolysis device according to FIG. 1.
Figure 3B:
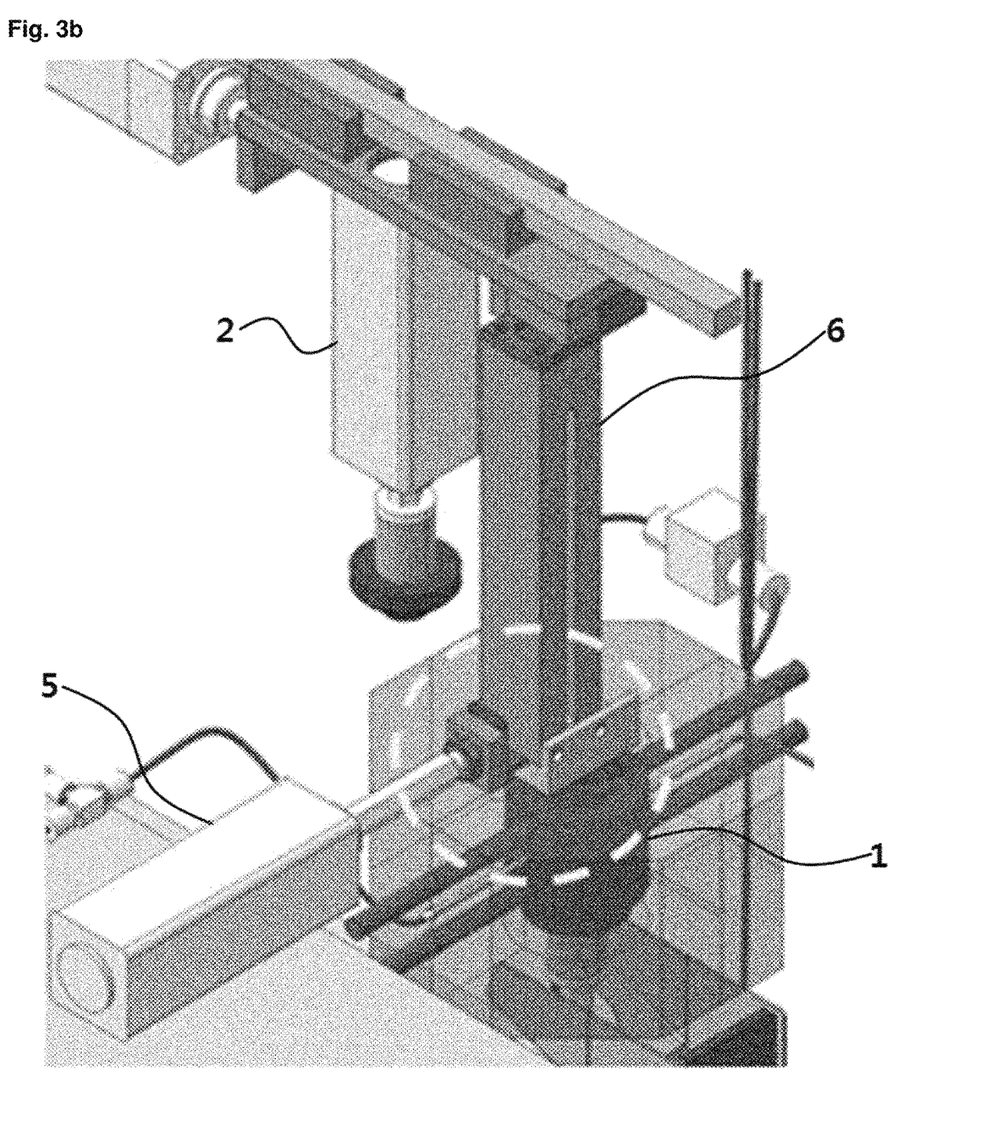

Referring to FIG. 3a and FIG. 3b, the transfer and storage of the sample (for example, coin cell battery) from the automatic sample supply member 6 to the reactor 1 will be described as follows. The order of sample transfer and storage of the automatic sample supply member 6 can be performed in the order of FIG. 3a to FIG. 3b. When the predetermined conditions (for example, predetermined time, etc.) are satisfied, the automatic sample supply member 6 moves above the reactor 1, and the sample injection unit 5 pushes the sample of the automatic sample supply member 6 into the reactor 1. Then, the reactor top member 2 moves above the upper end of the reactor 1, and the reactor top member 2 and the reactor bottom member 3 close the open upper and lower ends of the reactor 1 to shut off the outside air. In addition, for example, as one embodiment, when one end of the reactor bottom member 3 is located at the open upper end of the reactor 1, the other end of the reactor bottom member 3 is located inside or at the upper end of the reactor 1, and the sample is loaded on one end of the reactor bottom member 3, the reactor bottom member 3 moves vertically to the bottom so that one end of the reactor bottom member 3 close the open bottom of the reactor 1 and one end of the reactor top member 2 covers and seals the open top of the reactor 1. As another embodiment, when one end of the reactor bottom member 3 seals the open bottom of the reactor 1 and the sample is loaded inside the reactor 1, one end of the reactor top member 2 may cover and seal the open top of the reactor 1. To summarize, as described above, the sample is accommodated in the chamber sealed by the reactor 1, one end of the reactor top member 2 and one end of the reactor bottom member 3. The present invention is not limited to the above description and various modifications and changes can be made to the transfer of the sample from the automatic sample supply member 6 to the reactor 1 and the storage of the sample according to the various environments in which the present invention is implemented.

Figure 4A:
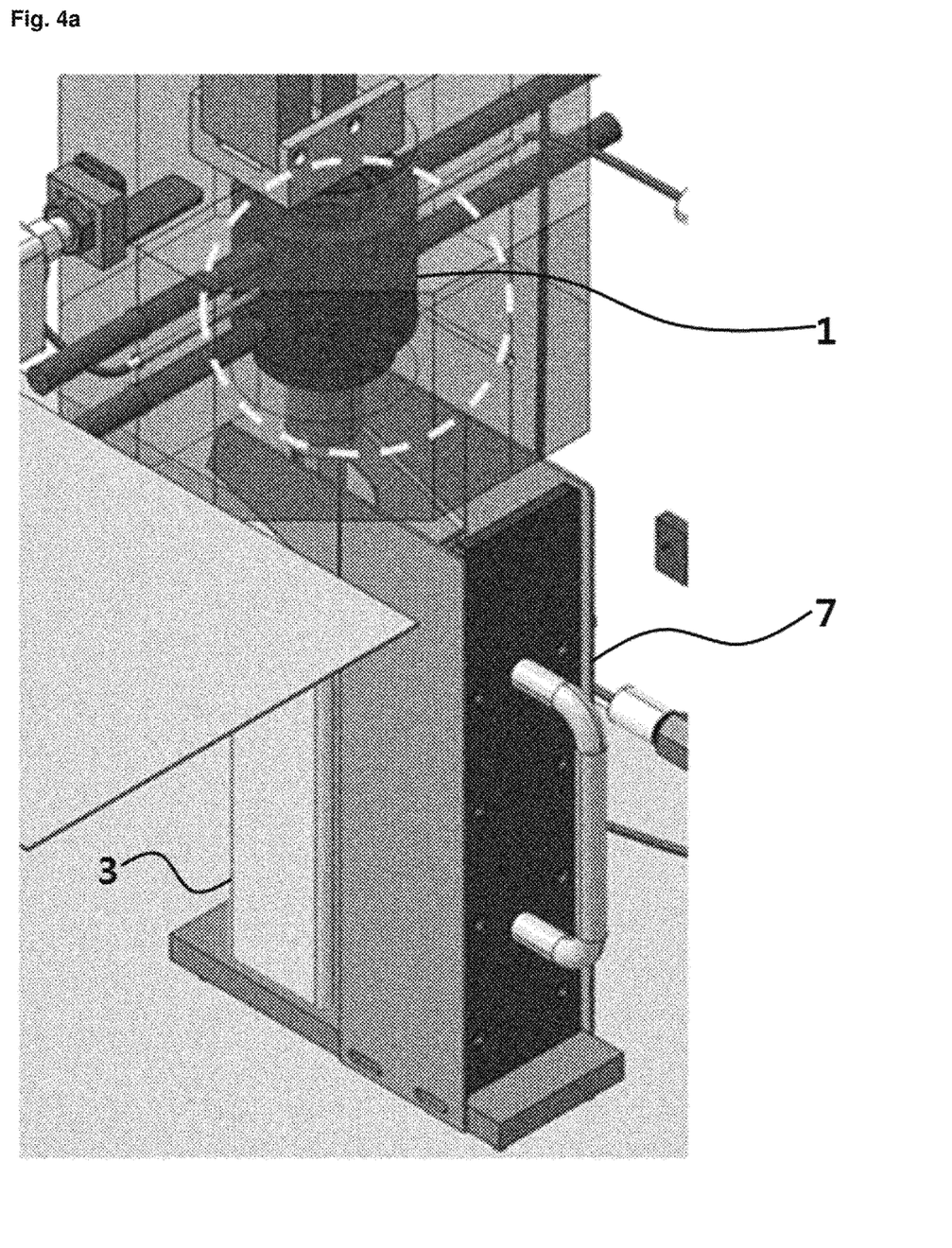
FIGS. 4a and 4b show a case of discarding a sample outside the reactor in the automated sample pyrolysis device according to the present invention.
Figure 4B:
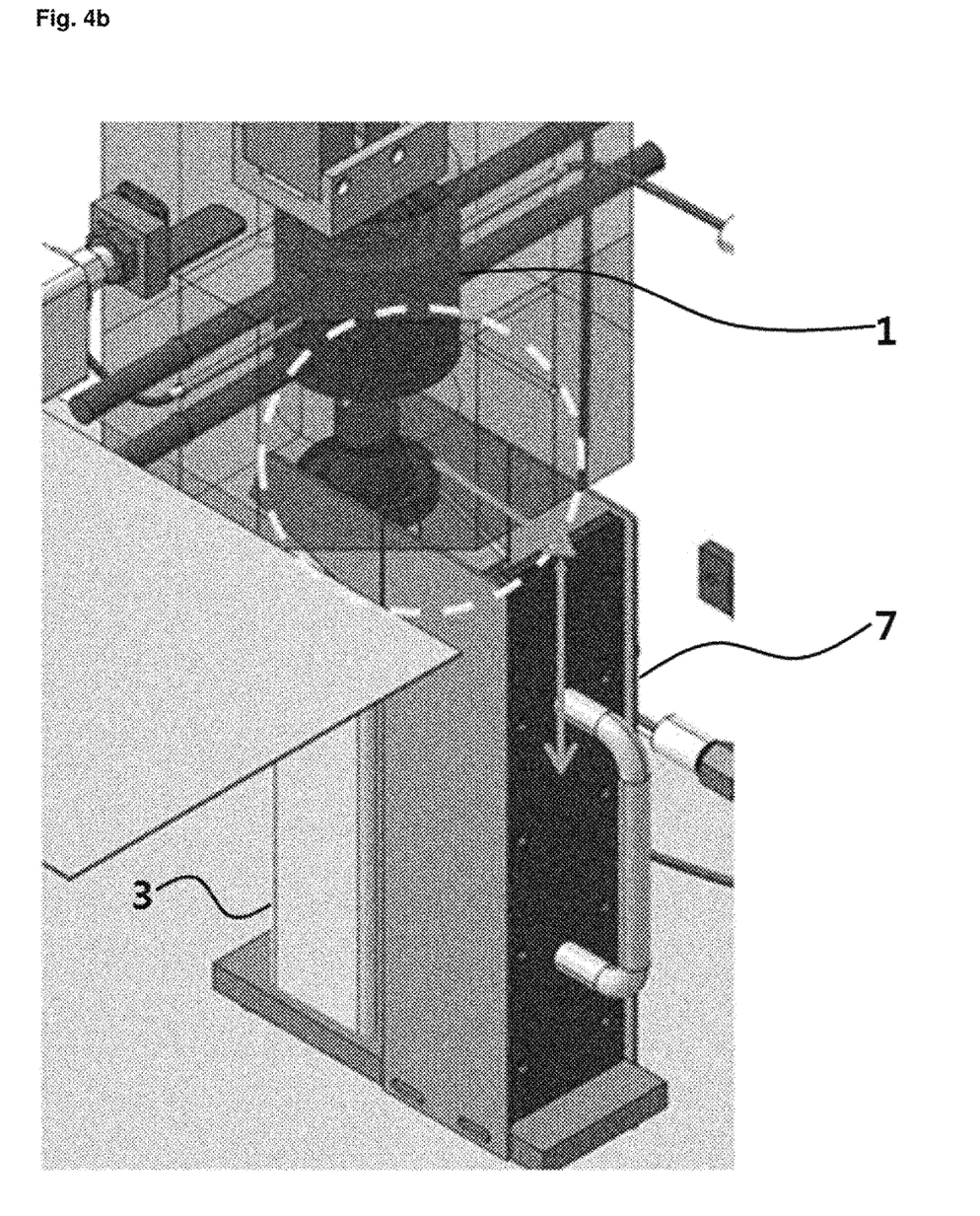

Further, referring to FIG. 4a and FIG. 4b, the transfer of the sample (for example, coin cell battery) from the reactor 1 to a waste part 7 and the discard of the sample will be described as follows. The transfer and discard of the sample can be performed in the order of FIG. 4a to FIG. 4b. As described later, when analyzing and collecting the gas generated by thermal decomposition of the sample is completed, the reactor bottom member 3 on which the sample is placed moves vertically downward from the reactor 1, one end of the reactor bottom member 3 on which the sample is placed is positioned at the inlet of the waster part 7 placed at the lower end of the reactor 1, and the sample is discarded into the waste part 7 in the direction shown by the arrow in FIG. 4b. For example, one end of the reactor bottom member 3 on which the sample is placed may be a slope so that the sample slips along the slope of one end of the reactor bottom member 3 and drops to the waste part 7 located at the bottom when the sample is discarded.

On the other hand, a carrier gas open/close means 9, a cooling gas open/close means 10, a vent open/close means 11 and an analyzer open/close means 12 can be connected to the reactor 1. Type or shape of each of the carrier gas open/close means 9, the cooling gas open/close means 10, the vent open/close means 11 and the analyzer open/close means 12 is not limited, and may be or may contain, for example, a valve. The carrier gas open/close means 9, the cooling gas open/close means 10, the vent open/close means 11 and the analyzer open/close means 12 can be implemented as, for example, a carrier gas valve, a cooling gas valve, a vent valve and an analyzer valve, respectively. The carrier gas open/close means 9 controls the flow of carrier gas into the reactor 1 by on/off. The carrier gas may be, for example, helium (He) gas. The carrier gas supply part (not shown) is connected to the reactor 1 via a mass flow controller (MFC) 8 and the carrier gas open/close means 9 by a pipe or a tube. That is, the mass flow controller 8 can be arranged between the reactor 1 and the carrier gas open/close means 9 in the flow path of the carrier gas. The mass flow controller 8 precisely controls the flow rate of the carrier gas supplied into the reactor 1. For example, the flow control range of the mass flow controller 8 may be 0 ml to 200 ml, the response speed from a main controller described later is within 1 second (for example, a response speed from the main controller having a touch panel is within 1 second), and the accuracy may be 1.0% (for example, if the flow rate to be controlled is 100 ml, the flow rate is controlled to 99 ml to 101 ml). Specifically, the carrier gas is supplied to the mass flow controller 8 from the carrier gas supply part, and the flow rate is controlled to a range of 0 ml to 200 ml as the carrier gas passes through the mass flow controller 8 (i.e., the opening and closing degree is controlled). Further, the carrier gas passing through the mass flow controller 8 is supplied to the reactor 1 via the open carrier gas open/close means 9. If the carrier gas open/close means 9 is closed, the carrier gas is not supplied to the reactor 1.

Further, the vent open/close means 11 controls discharge of the gas in the reactor 1 (for example, the gas in the reactor 1, the gas generated from the sample, etc.), i.e., discharge from the reactor 1 to the cooling gas vent (not shown) by on/off. The reactor 1 is connected to the vent outside the automated sample pyrolysis device 100 via the vent open/close means 11 and a vent gas regulator (not shown) by a pipe or a tube. Specifically, the gas in the reactor 1 passes through the open vent open/close means 11 and then the vent gas regulator so as to be discharged to the outside through the vent. That is, the vent gas regulator may be provided between the reactor 1 and the vent open/close means 11 in the flow path through which the gas in the reactor 1 is discharged to the outside. The vent gas regulator can be, for example, a pressure regulator that can control the flow rate of the vent gas, and the pressure setting range can be from 0.02 Mpa to 0.2 Mpa and the maximum supply pressure can be 1.0 Mpa. In summary, the vent open/close means 11 controls opening and closing, and the vent gas regulator controls the amount of the gas discharged to the outside.

Further, the analyzer open/close means 12 controls the flow of the gas generated in the sample and the carrier gas to a gas analyzer or a gas collector (not shown) by on/off. The reactor 1 can be connected to the gas analyzer or the gas collector (not shown) via a condenser 13 and the analyzer open/close means 12 by a pipe or a tube and the like. The gas analyzer may be, for example, a device in which a EGA equipment is equipped with a MS apparatus, a GC apparatus or a IR (FT-IR, NIR) together with various gas sensors ($O_2$ sensor, $CO_2$ sensor, etc.) and a laser analyzer (for oxygen analysis) and the like. The condenser 13 may be made of a material, for example, stainless steel (as one embodiment, SUS (steel use stainless) 304, SUS 310, etc,) and may be an air cooling gas cooling device.

Further, the cooling gas open/close means 10 controls the flow of the cooling gas into the reactor 1 by on/off. The cooling gas can be supplied into the reactor 1 to cool the temperature (for example, to cool to room temperature) of the reactor and the furnace 4 when the gas is introduced into the gas analyzer for analyzing the gas generated by pyrolysis of the sample in the reactor 1 or into the gas collector for collecting the gas. The cooling gas may be, for example, inert gas (He, etc.), nitrogen ($N_2$) gas or air. A cooling gas supply part (not shown) is connected to the reactor 1 via the cooling gas open/close means 10 by a pipe or a tube.

The carrier gas open/close means 9 and the cooling gas open/close means 10 described above control the flow of the gas, respectively, can be made of, for example, stainless steel (as one embodiment, SUS 316), and the maximum working pressure can be 250 psi. Further, the vent open/close means 11 and the analyzer open/close means 12 described above control the flow direction of the gas, respectively, can be made of, for example, stainless steel (as one embodiment, SUS 316), and the maximum working pressure can be 250 psi.

The manner in which the operation of the automated sample pyrolysis device 100 according to the present invention is automatically controlled will be described.

Transfer and Storage of Sample to Reactor 1

First, when a start button on the touch panel is pressed, the automated sample pyrolysis device 100 is in standby mode until the temperature of the furnace 4 reaches the experiment starting temperature. Then, when the reactor top member 2 located on top of the reactor 1 moves up vertically, the automatic sample supply member 6 moves to above the reactor 1 and the sample injection unit 5 pushes the sample of the automatic sample supply member 6 into the reactor 1. Then, the reactor top member 2 moves above the top of the reactor 1 and the reactor top member 2 and the reactor bottom member 3 close the open upper and lower ends of the reactor 1 to shut off the outside air. For more detailed description, refer to the description given above with reference to FIG. 3a and FIG. 3b.

Replacement with Carrier Gas in Reactor 1

After the sample is accommodated in the reactor 1 and the inside of the reactor 1 is sealed, the carrier gas open/close means 9 is opened (on), the vent open/close means 11 is opened, the carrier gas is supplied into the reactor 1 from the carrier gas supply part (not shown), and then the air inside the reactor 1 is replaced with the carrier gas. At this time, the cooling gas open/close means 9 and the analyzer open/close means 12 are kept in a closed state. In some cases, if the vent open/close means 11 is in a closed state and the analyzer open/close means 12 is in an open state, the gas analyzer or the gas collector may not be connected to the analyzer open/close means 12 so that the gas in the reactor 1 can be discharged via the analyzer open/close means 12.

On the other hand, when the predetermined condition is satisfied, for example, when the predetermined time elapses from the start of the supply of the carrier gas into the reactor 1, the replacement of the internal air of the reactor 1 with the carrier gas is completed, and the subsequent process is automatically performed. The predetermined time from the start of the supply of the carrier gas can be variously changed according to the environment in which the present invention is implemented. As one embodiment, since the time for replacing the air in the reactor 1 with the carrier gas differs depending on the internal volume of the reactor 1 and the like, the predetermined time from the start of the supply of the carrier gas may be controlled depending on the internal volume of the reactor 1 and the like. For example, when the internal volume of the reactor 1 is 20 ml, the vent open/close means 11 can be switched to a closed state 10 minutes after the start of the supply of the carrier gas (i.e., predetermined time). In other words, the volume of the reactor 1 may be, for example, 20 ml, but it can be applied variously by changing the design, and the supply time of the carrier gas can be set variously from several seconds (sec) to several hours.

Start of Analysis or Collection of Gas Generated From Pyrolysis of Sample

As one embodiment, in the above-described process of replacing the air in the reactor 1 with the carrier gas, when the predetermined condition is satisfied, for example, when the predetermined time elapses from the start of the supply of the carrier gas, the carrier gas open/close means 9 and the vent open/close means 11 are automatically closed and the furnace 4 is heated to the first predetermined temperature. Then, when the predetermined condition is satisfied, for example, when the predetermined time elapses from the start of the supply of the carrier gas or the furnace 4 reaches the first predetermined temperature (for example, 300° C.), the carrier gas open/close means 9 and the analyzer open/close means 12 are automatically open and the carrier gas is supplied into the reactor 1 via the carrier gas open/close means 9. Then, the gas generated from the pyrolysis of the sample in the reactor 1 and the carrier gas are supplied into the gas analyzer or the gas collector via the analyzer open/close means 12. At this time, the cooling gas open/close means 10 is kept in a closed state.

As another embodiment, in the above-described process of replacing the air in the reactor 1 with the carrier gas, when the predetermined condition is satisfied, for example, when the predetermined time elapses from the start of the supply of the carrier gas, the analyzer open/close means 12 is automatically open and the vent open/close means 11 is closed at the same time. Accordingly, the carrier gas is continuously supplied into the reactor 1 via the carrier gas open/close means 9, and the gas generated from the pyrolysis of the sample in the reactor 1 and the carrier gas are supplied to the gas analyzer or the gas collector via the analyzer open/close means 12. Similarly, at this time, the cooling gas open/close means 10 is kept in a closed state.

For more specific example, first, when the predetermined condition is satisfied, for example, when the predetermined time elapses from the start of the supply of the carrier gas, the carrier gas open/close means 9 and the vent open/close means 11 are automatically closed and the temperature of the furnace 4 is raised. Then, the first predetermined temperature (for example, 300° C.) is satisfied, the carrier gas open/close means 9 and the analyzer open/close means 12 are automatically open and the gas generated from the pyrolysis of the sample in the reactor 1 and the carrier gas are supplied to the gas analyzer or the gas collector.

Secondly, when the predetermined condition is satisfied, for example, when the predetermined time elapses from the start of the supply of the carrier gas, the vent open/close means 11 is automatically closed and the analyzer open/close means 12 is open while the carrier gas open/close means 9 is kept in an open state. Then, the gas generated from the pyrolysis of the sample in the reactor 1 and the carrier gas are supplied to the gas analyzer or the gas collector.

Third, analysis or collection of the gas generated from the pyrolysis of the sample may be carried out by more subdivided sections. When the predetermined condition is satisfied, for example, when the predetermined time elapses from the start of the supply of the carrier gas, the vent open/close means 11 is automatically closed and the analyzer open/close means 12 is open while the carrier gas open/close means 9 is kept in an open state. Then, the gas generated from the pyrolysis of the sample in the reactor 1 and the carrier gas are supplied to the gas analyzer or the gas collector. Then, the second predetermined temperature (for example, 150° C.) is satisfied, the carrier gas open/close means 9 and the analyzer open/close means 12 are automatically closed while the temperature of the furnace 4 is raised. Then, when the predetermined condition is satisfied, for example, when the third predetermined temperature (for example, 300° C.) is satisfied, the carrier gas open/close means 9 and the analyzer open/close means 12 are automatically open and the gas generated from the pyrolysis of the sample in the reactor 1 and the carrier gas are supplied to the gas analyzer or the gas collector. Then, when the predetermined condition is satisfied, for example, when the fourth predetermined temperature (for example, 400° C.) is satisfied, the carrier gas open/close means 9 and the analyzer open/close means 12 are automatically closed while the temperature of the furnace 4 is raised. Then, when the predetermined condition is satisfied, for example, when the fifth predetermined temperature (for example, 600° C.) is satisfied, the carrier gas open/close means 9 and the analyzer open/close means 12 are automatically open and the gas generated from the pyrolysis of the sample in the reactor 1 and the carrier gas are supplied to the gas analyzer or the gas collector.

Stop of Analysis or Collection of Gas Generated From Pyrolysis of Sample

When the predetermined condition is satisfied after the analysis and the collection of the gas generated from the pyrolysis of the sample is proceeded as described above, for example, when the temperature of the furnace 4 reaches the sixth predetermined temperature, i.e., when the stop temperature of the analysis and the collection of the gas generated from the pyrolysis of the sample is satisfied, the carrier gas open/close means 9 and the analyzer open/close means 12 are closed (off). At the same time, the cooling gas open/close means 10 and the vent open/close means 11 are open (on). Accordingly, since the carrier gas open/close means 9 and the analyzer open/close means 12 are closed, the carrier gas is no longer supplied into the reactor 1 and the gas generated from the sample is no longer supplied to the gas analyzer or the gas collector. Instead, the cooling gas flows from the cooling gas supply part (not shown) into the reactor 1 via the cooling gas open/close means 10 to lower the temperature of the reactor 1 and the furnace 4, and the gas is discharged from the reactor 1 in the reactor containing the cooling gas to the outside of the automated sample pyrolysis device 100 via the vent open/close means 11 through the vent (not shown).

Discard of Sample From Reactor 1

The transfer and the discard of the sample (for example, coin cell battery) from the reactor 1 to the waste part 7 will be described as follows. As described later, when the analysis or the collection of the gas generated from the pyrolysis of the sample is completed, the reactor bottom member 3 on which the sample is placed moves down vertically from the reactor 1 and one end of the reactor bottom member 3 on which the sample is placed is located at the inlet of the waste part 7 located at the bottom of the reactor 1, and the sample is discarded into the waste part 7 in the direction shown by an arrow in FIG. 4b.

On the other hand, the above-described predetermined temperatures may be set based on the temperature of the furnace 4 as described above, but may be set based on the temperature inside the reactor 1 in some cases. Further, the above-described predetermined temperatures are preset in the main controller connected to the automated sample pyrolysis device and the automated sample pyrolysis device 100 can be operated in the manner described above when the temperature sensed by the temperature sensor installed in the furnace 4 reaches this predetermined temperature. Similarly, a supply time point and a supply interval and the like of the sample (for, example, battery) of the automatic sample supply member 6 may be preset in the controller or a control unit. Or the automatic sample supply member 6 may automatically supply the sample to the sample injection unit 5 when the sensor installed in the waste part 7 detects that a battery is stored in the waste part 7. Further, an operator may manually control the automated sample pyrolysis device 100 through the main controller according to various environments in which the present invention is implemented, for example, analysis conditions and time of the gas generated in the sample.

In this regard, the automated sample pyrolysis device 100 according to one embodiment of the present invention and the main controller connected thereto will be described in detail. The main controller contains a touch panel-type display.

The operator can touch the panel to pre-enter the conditions for the automated operation of the automated sample pyrolysis device 100, or the automated sample pyrolysis device 100 may be automatically operated according to a preset method, or the automated sample pyrolysis device 100 can be manually controlled by touching the panel.

The touch panel-type display can be used to set the preset temperatures, to set the flow rate of the mass flow controller and to set the number of the sample. The preset temperature of the furnace 4, the setting of the flow rate of the mass flow controller 8 and the setting of the number of the sample are called "Method", and each "Method" can be stored up to four. By changing the color of each button on the screen displayed during operation, it is possible to check whether each component of the automated sample pyrolysis device 100 operates.

According to the present invention, the gas generated inside can be collected and measured by heating the sample (battery itself) according to the thermal behavior (i.e., temperature rising, isothermal temperature, etc.) of the battery, and a series of such processes for collecting and measuring the gas generated in the sample (battery) is automated. That is, the automated sample pyrolysis device 100 according to the present invention is a device that comprises a system including a plurality of opening and closing means, a furnace, a reactor and a temperature control system for collecting and measuring the gas generated in the sample according to the thermal behavior of the battery by heating the sample (battery itself) and in which these components are automatically controlled, and it corresponds to an automated system that can sequentially evaluate a plurality of a secondary battery. In summary, the device is integrated with Accelerating Rate Calorimeter (ARC) function, Evolved gas analysis (EGA) function and automated function. This is entirely different from the conventional secondary battery-generated gas collecting devices and collection methods. In other words, the safety evaluation device such as the conventional ARC only evaluates the endothermic and exothermic reactions, but the device according to the present invention is capable of analyzing the chemical reaction during the thermal behavior of the sample by an automatic control method by confirming the gas (EGA) generated by heating or isotherming the sample like ARC.

Further, the present invention enables the gas generated according to the thermal behavior of the sample (battery) to be collected and more precisely analyzed in real time while safely protecting the operator from the danger of battery ignition or explosion. In addition, it has an advantage of collecting or analyzing all the gas generated from the battery such as an electrolytic decomposition gas as well as $O_2$, $CO_2$, $H_2O$ and CO generated from the sample (electrode material).

Further, shape, arrangement, material, and the like of each component of the automated sample pyrolysis device 100 according to the present invention are not limited to those shown in FIGS. 1 and 2 and the description thereof, and various modifications and changes may be made to the various environments in which the present invention is implemented. Further, the device for analyzing the gas generated inside the battery by using, for example, a battery (secondary battery, coin cell) as a sample is described However, the present invention is not limited thereto, and it can be used for heating other samples, and collecting and measuring the gas generated. Further, the term 'connection" used herein includes cases where each component is connected directly and indirectly through another component.

It should be understood that those skilled in the art can carry out other modifications without changing its technical spirit or essential features. Therefore, the above-described embodiment of the present invention is merely exemplary in all aspects and should not be construed to be limited, and it should be understood that the scope of the present invention is defined by the following claims and the meanings and ranges of the claims and all modifications and changed forms derived from their equivalents pertain to the scope of the present invention.

INDUSTRIAL AVAILABILITY

According to the present invention, it is possible to collect or analyze the gas generated in a sample (for example, battery itself) according to the thermal behavior of the sample, and the process of pyrolyzing the sample (battery itself) to collect and measure the gas generated in the battery is automated. This is, quite different from the conventional devices and methods for collecting the gas generated in a secondary battery. It can collect the gas generated in the sample (battery) according to the thermal behavior of the sample and analyze it more precisely in real time, and it has the advantage of safely protecting the operators from the danger of battery ignition or explosion. In addition, it has an advantage of collecting or analyzing all the gas generated in the sample (battery) such as electrolytic decomposition gas as well as $O_2$, $CO_2$, $H_2O$ and CO generated in the sample (battery material).

The invention claimed is:

1. An automated sample pyrolysis device, adapted to be connected to a front of a gas analyzer or gas collector to collect or analyze gas generated by heating of a sample, comprising: a reactor configured to accommodate the sample therein, upper and lower ends of the reactor each having a respective opening, the reactor having a reactor top member and a reactor bottom member configured to vertically transfer the sample, the reactor top member and the reactor bottom member being vertically movable through the openings of the upper and lower ends, respectively, one end of the reactor top member and one end of the reactor bottom member being configured to seal the reactor, one end of the reactor top member, and one end of the reactor bottom member together configured to be a sealed chamber; an automatic sample supply member configured to store the sample and to automatically supply the sample to the reactor, the sample being at least one battery; a sample injection unit configured to transfer the sample from the automatic sample supply member to the reactor; a waste part located at a bottom of the sample pyrolysis device, one end of the reactor bottom member being positioned at an inlet of the waste part and having a surface that is sloped relative to the bottom of the sample pyrolysis device; a furnace capable of surrounding the reactor and capable of heating the sample; and a main controller configured to automatically: control a supply of a carrier gas into the reactor from a start of operation of the automated sample pyrolysis device until a first predetermined condition is satisfied, when a second predetermined condition is satisfied, control a supply of the gas generated by heating of the sample to the gas analyzer or the gas collector, when a third predetermined condition is satisfied, control both the supply of the carrier gas into the reactor and the supply of the gas generated by heating of the sample in the reactor to the gas analyzer or the gas collector to be stopped, wherein the reactor bottom member is configured such that the sample deposited thereon slips along the sloped surface of the one end of the reactor bottom member and drops to the waste part.

2. The automated sample pyrolysis device according to claim 1, which further comprises:
a carrier gas open/close means switchable between an open state and a closed state for controlling entry of the carrier gas into the reactor;
an analyzer open/close means switchable between an open state and a closed state for controlling a flow of gas from the reactor into the gas analyzer or the gas collector; and
a vent open/close means switchable between an open state and a closed state for regulating a discharge of gas from the reactor to outside of the automated sample pyrolysis device.

3. The automated sample pyrolysis device according to claim 2, wherein the main controller is configured to control the carrier gas open/close means and the vent open/close means to be in the open state, and the analyzer open/close means to be in the closed state, from the start of operation of the automated sample pyrolysis device until the first predetermined condition is satisfied, and
the main controller is configured to switch the vent open/close means to the closed state when the first predetermined condition is satisfied.

4. The automated sample pyrolysis device according to claim 3, wherein the main controller is configured to switch the carrier gas open/close means to the closed state when the first predetermined condition is satisfied, and
the main controller is configured to switch the carrier gas open/close means and the analyzer open/close means to the open state when the second predetermined condition is satisfied.

5. The automated sample pyrolysis device according to claim 3, wherein the first predetermined condition and the second predetermined condition are the same, and
the main controller is configured to maintain the carrier gas open/close means in the open state and to switch the analyzer open/close means to the open state when the first predetermined condition is satisfied.

6. The automated sample pyrolysis device according to claim 4, wherein the main controller is configured to switch the carrier gas open/close means and the analyzer open/close means to the closed state, and to switch the vent open/close means to the open state when the third predetermined condition is satisfied.

7. The automated sample pyrolysis device according to claim 6, which further comprises a cooling gas open/close means for controlling a flow of cooling gas to the reactor for cooling the reactor, and
the main controller is configured to switch the cooling gas open/close means to the open state when the third predetermined condition is satisfied.

8. The automated sample pyrolysis device according to claim 2, which further comprises a mass flow controller, located between the reactor and the carrier gas open/close means, for controlling a flow rate of the carrier gas supplied to the reactor.

9. The automated sample pyrolysis device according to claim 2, which further comprises a vent gas regulator, located between the reactor and the vent open/close means, for regulating a flow rate of the discharge of gas from the reactor to outside of the automated sample pyrolysis device.

10. The automated sample pyrolysis device according to claim 1, wherein one end of each of the reactor top member and the reactor bottom member is coupled to a spring, and each of the reactor top member and the reactor bottom member is vertically movable by an air cylinder connected to the spring.

11. The automated sample pyrolysis device according to claim 7, which further comprises a condenser, located between the reactor and the cooling gas open/close means, for cooling the gas in the reactor discharged from the reactor to the outside of the automated sample pyrolysis device.

\* \* \* \* \*